(12) United States Patent
Tan et al.

(10) Patent No.: US 6,787,016 B2
(45) Date of Patent: Sep. 7, 2004

(54) DYNAMIC COATING WITH LINEAR POLYMER MIXTURE FOR ELECTROPHORESIS

(75) Inventors: Hongdong Roy Tan, San Jose, CA (US); Alexander Sassi, Berkeley, CA (US); Ingrid Cruzado, San Jose, CA (US)

(73) Assignee: Aclara Biosciences, Inc., Mountain View, CA (US)

(*) Notice: Subject to any disclaimer, the term of this patent is extended or adjusted under 35 U.S.C. 154(b) by 355 days.

(21) Appl. No.: 09/847,780

(22) Filed: May 1, 2001

(65) Prior Publication Data

US 2002/0029968 A1 Mar. 14, 2002

Related U.S. Application Data

(60) Provisional application No. 60/201,575, filed on May 1, 2000.

(51) Int. Cl.⁷ .................. G01N 27/447; G01N 27/453
(52) U.S. Cl. .................. 204/455; 204/469; 204/605
(58) Field of Search .................. 204/451, 455, 204/468, 469, 460, 456, 606, 616

(56) References Cited

U.S. PATENT DOCUMENTS

| | | | |
|---|---|---|---|
| 5,545,302 A | 8/1996 | Zhu | 204/454 |
| 5,552,028 A | 9/1996 | Madabhushi | 204/451 |
| 5,567,292 A | 10/1996 | Madabhushi | 204/451 |
| 5,916,426 A | 6/1999 | Madabhushi | 204/451 |
| 5,948,227 A | 9/1999 | Dubrow | 204/455 |
| 6,042,710 A | 3/2000 | Dubrow | 204/454 |
| 6,056,860 A | 5/2000 | Amigo | 204/454 |
| 6,074,541 A | 6/2000 | Srinivasan | 204/451 |
| 6,074,542 A | 6/2000 | Dolnik | 204/454 |
| 6,117,293 A | 9/2000 | Zhang | 204/455 |
| 6,322,682 B1 | 11/2001 | Arvidsson | 204/454 |

OTHER PUBLICATIONS

Hong et al. (Improved Resolution in the Capillary Electrophoretic Separation of DNA Fragments by USing Mixed Polymer Matrix with Hydroxycellulose and Polyvinylpyrolidone, Fenxi Keue Xuebao (1999). 15(6), 441–445). Only the abstract is in English.*

Page 1304 of the Concise Encyclopedia of Polymer Science and Engineering, ed. J. Kroschwitz, 1990.*

Page 2 of Water–Soluble Cellulose Ethers for Hair Care Products, by Mary Clarke, Hercules Reprint SOFW 17/1990.*

Hjerten, S. "High–Performance Electrophoresis Elimination of Electroendosmosis and Solute Adsorption," J. Chromatography A, (1985), 347:191–198.

Chiari, M. et al. "New types of separation matrices for electrophoresis." Electrophoresis (1995), 16:1815–1829.

Iki, N. "Non–bonded poly(ethylene oxide) polymer–coated column for protein separation by capillary electrophoresis", J. Chromatography A (1996), 731:273–282.

Swerdlow, H. "Stability of capillary gels for automated sequencing of DNA" Electrophoresis (1992), 13:475–483.

* cited by examiner

*Primary Examiner*—Alex Noguerola
(74) *Attorney, Agent, or Firm*—Stephen C. Macevicz; David Albagli

(57) ABSTRACT

Compositions and methods are provided for performing capillary electrophoresis using a composition comprising in combination in an aqueous buffered medium a coating polymer and a sieving polymer, where the sieving polymer is more hydrophilic than the coating polymer and is present in greater amount. Of particular interest are uncrosslinked acrylamide polymer mixtures for coating plastic channels and providing sieving for performing DNA separations in microfluidic devices. Polyacrylamide or N,N-dimethyl acrylamide is used with a N,N-dialkyl acrylamide copolymer, either separately or together for sieving and coating, serving as the medium in capillary electrophoresis DNA separations.

15 Claims, 9 Drawing Sheets

Time (s)

DYNAMIC COATING WITH LINEAR POLYMER MIXTURE FOR ELECTROPHORESIS

This application claims the benefit of U.S. Provisional Application No. 60/201,575, filed May 1, 2000, which is incorporated herein by reference in its entirety.

TECHNICAL FIELD

The field of this invention is electrophoretic separation using polymer-containing media.

BACKGROUND OF THE INVENTION

Capillary electrophoresis is one of the most widely used separation techniques in the biologically related sciences. It finds application in genetics, for DNA sequencing, single nucleotide polymorphism ("snp") detection, identification of sequences, gene profiling, etc.; in drug screening, particularly high throughput drug screening, where the electrophoresis allows for the use of impure reagents, separation of entities that can interfere with detection of a signal, particularly an electromagnetic signal; for performing reactions by bringing together reactants and allowing for their automated separation, segregation, purification and analysis without manual intervention, and the like. Due to the highly efficient heat dissipation, capillary electrophoresis permits rapid and efficient separations of charged substances. Charged substances will be subject to two electromigrating forces under the influence of the applied electrical potential at both ends of the capillary. One is the electrophoretic mobility component, which depends on the charge and size of the entity and the electrical field strength. The other is the electroendosmotic flow ("EOF") providing a fixed bulk velocity component, which drives both neutral species and ionic species, regardless of mobility, towards an electrode in relation to the charge on the wall of the capillary.

The magnitude of EOF is highly dependent on the surface charge and viscosity near the surface of the capillary. These properties are affected by the material of the capillary wall, the buffer or medium composition and the pH. In the case of a silica capillary, upon ionization the negatively charged inner wall attracts a layer of positive ions from the buffer. As these mobile ions flow toward the cathode under the influence of the electrical potential, the bulk solution also flows in this direction to maintain electroneutrality. Control and suppression of EOF improves the separation resolution in such situations as capillary zone electrophoresis, capillary isoelectrofocusing and capillary gel electrophoresis. Failure to suppress the EOF can result in inadequate separations, especially with nucleic acids and proteinaceous materials.

With the inception of microfabricated devices used as the structure to carry out electrophoresis inside a microchannel, particularly where the device is composed of plastic, plastics may vary as the amount of wall charge, the adverse effect of EOF may be amplified. Many plastic materials are attractive for manufacturing large numbers of microfabricated devices, since molds can be produced with intricate designs of interconnected channels and reservoirs. These molds may then be used for the precise fabrication of the microfabricated devices rapidly and inexpensively. Various materials which find use include the polymethacrylates and other acrylics, polycarbonates, dimethylsiloxanes, polyalkenes, etc. Each of these polymers will have a different surface chemistry.

Based on the experience with fused silica, the silanol Si—OH ionized from the silica surface produces a negative charged surface. A diversity of treatments has been developed for suppressing the EOF in silica capillaries to minimize the interaction between the species to be analyzed and the capillary inner wall. The underlying idea is to reduce the production of charges. With the development of plastic devices, new approaches are required to modify the plastic surface to diminish EOF. The EOF may be attributed to the plastic composition and the nature of the plastic surface, where the plastic surface is conditioned by the polymerization process and the forming or production conditions of the device.

To suppress both electro osmotic flow as well as DNA-capillary wall interactions, in DNA sequencing using electrophoresis, control of the capillary inner surface is required for hydrophobic sieving polymers, such as polyacrylamide and hydroxyethylcellulose. Both permanently covalent and dynamically temporal modification of the inner surface can be applied. However, the procedures to produce covalent coatings are often complicated and time-consuming and the coatings may be subject to chemical instability over extended use. In order to reduce DNA sequencing cost, improve the reproducibility and reliability, it is therefore desirable to replace the expensive and often unreliable covalent coatings with adsorbed coatings.

BRIEF DESCRIPTION OF THE PRIOR ART

References of interest include U.S. Pat. Nos. 4,865,707; 5,112,460; 5,663,129; 5,832,785, and 5,840,338. References of interest include Karger, et al., Anal. Chem. 1998, 70, 3996–4003; Fung, et al., ibid, 1999, 71, 566–573; and Madabhushi, Electrophoresis, 1998, 19, 224–230.

SUMMARY OF THE INVENTION

Compositions and methods for performing capillary electrophoresis, particularly in polymer-substrate microfluidic devices, are provided employing a mixed uncrosslinked polymer composition, which serves as both a coating reagent and sieving media in a microfluidic device. The polymeric composition comprises a mixture of polymers, where the more hydrophilic polymers serve primarily as sieving polymers and the less hydrophilic polymers serve primarily as coating polymers. Of particular interest is the use of uncrosslinked polyacrylamide and N-substituted polyacrylamide with varying hydrophilicity as a result of varying the substituents on the amide nitrogen. Particularly, alkyl substituents are used of varying chain length. By appropriate selection, one can tune the hydrophilicity of one component for the best coating results, while controlling the other component(s) for the best sieving effect. The polymeric composition or the coating component thereof may be included in the media used in the microfluidic device channel prior to the electrophoretic process or the composition or only the sieving component may be included during the electrophoretic separation after application of the coating component with greatly enhanced separation of charged entities.

DETAILED DESCRIPTION OF THE INVENTION

Polymer compositions, formulations comprising the polymer compositions and their use in conjunction with microfluidic devices, particularly polymer-substrate microfluidics devices, for electrophoretic processes are provided. Also provided is a microfluidics device having a separation channel containing the novel polymer composition.

A. Microfluidics device

The microfluidics device typically includes a polymer substrate having a channel network formed therein, typically a polymer substrate having a channel network providing (i) a supply channel for holding a sample, (ii) a drain channel, and (iii) a separation channel for containing an electrolyte buffer, and the polymer composition of the invention. The channels are supplied liquid during an electrophoretic operation from reservoirs connected to the ends of the channels. In addition, sample may be injected into the separation channel from the supply channel by conventional sample injection means applicable to microfluidics devices.

Figure 8A:
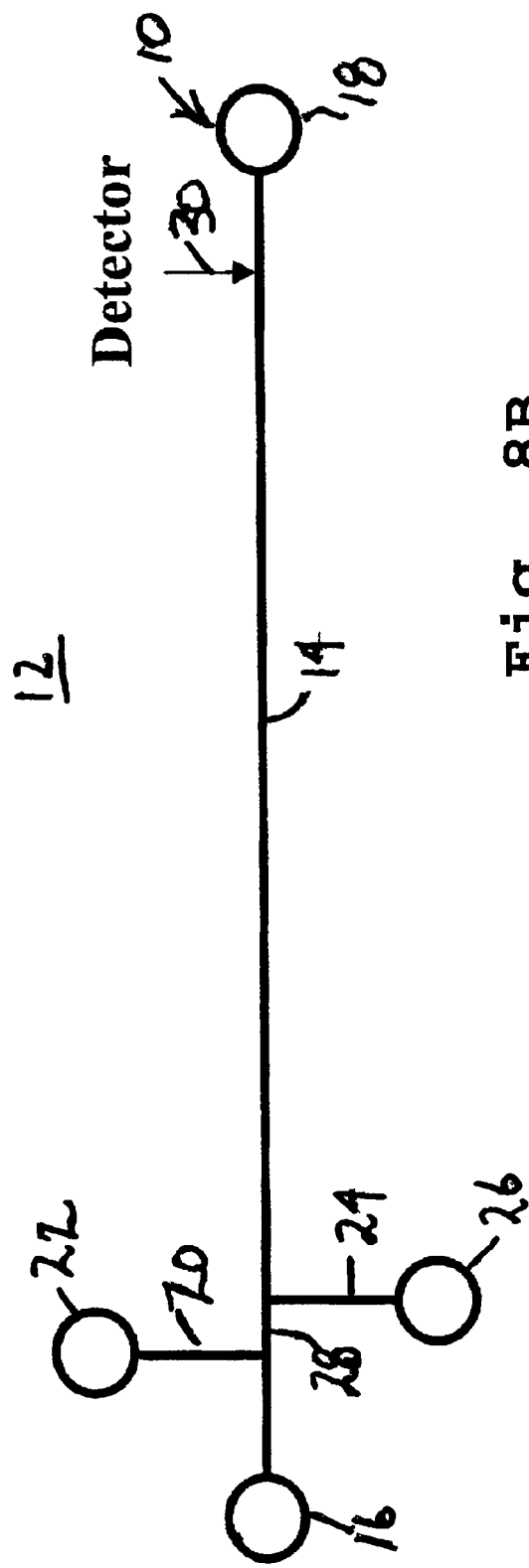
FIGS. 8A and 8B are a plan view of the channel network used in obtaining the data provided in the other figures (FIG. 8A), and showing channel corss-section in the network (FIG. 8B).
Figure 8B:
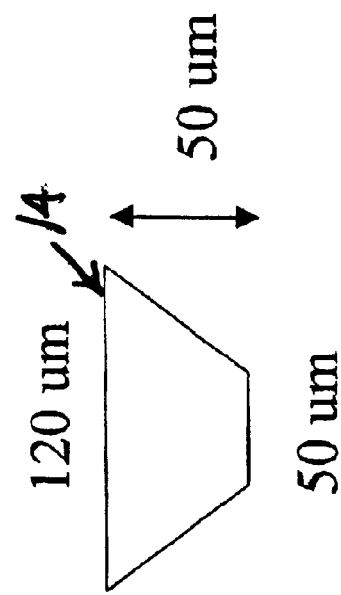

A typical device channel network 10 in a microfluidics device 12 is shown in FIG. 8A. The network includes a main separation channel 14 terminating at a buffer reservoir 16 and a downstream waste reservoir 18. An exemplary separation channel has the cross-sectional shape and dimensions shown in FIG. 8B. Sample material is supplied to the separation channel reservoir through a supply channel 20, from a sample-supply reservoir 22. A second waste reservoir 26 communicates with the separation channel through a third channel 24.

Each of the reservoirs is provided with an electrode (not shown) through which a selected voltage potential is applied across selected reservoirs by a suitable voltage source. In particular, to load a sample from reservoir 22 into the separation channel, a voltage is applied across reservoirs 22, 24, to draw sample material into and through the separation channel, between the two reservoirs. This loads sample in the sample volume 28 in the segment of channel 14 between channels 20, 24. To effect separation of the sample material along the separation channel 14, which is filled with the composition of the invention, a suitable voltage potential is applied across reservoirs 16, 18, causing sample material, e.g., nucleic acid fragments, to migrate from the sample volume region downstream in channel 14. Band migration in the channel is detected by a detector indicated at 30.

The microfluidics device is typically formed on and contains a substrate or card in which the microstructures, primarily channels and reservoirs, are present. The substrate may be of any convenient material, such as glass, polymer (plastic), silicon, fused silica, or the like, and preferably, a polymer substrate. Illustrative polymers include methyl methacrylate and copolymers thereof, dimethylsiloxanes, polystyrene, and polycarbonate. Preferred polymers are PMMA (polymethylmethacrylate) and cyclic olefin homopolymer or co-polymer thermoplastics derived from ring-shaped norbornene molecules. The latter polymers, such as described in U.S. Pat. Nos. 5,561,208, 5,462,995, and 5,334,424, are characterized by very low fluorescence emission, and thus are suitable for detecting electrophoretic bands by fluorescence emission. Preferred polymers of this type include Zeonex and Zeonor trade-name polymers, such as Zeonor 1420, manufactured by Zeon Corporation (Louisville, Ky.).

The capillary channels may vary as to dimensions, width, depth and cross-section, as well as shape, being rounded, trapezoidal, rectangular, etc. The path of the channels may be straight, rounded, serpentine, meet at corners, cross-intersect, meet at tees, or the like. The channel dimensions will generally be in the range of about 0.1 $\mu$m to 1 mm deep and about 0.5 $\mu$m to 500 $\mu$m wide, where the cross-sectional area will generally be 0.1 $\mu m^2$ to about 0.25 $mm^2$. The channel lengths will vary widely depending on the operation for which the channel is to be used. The separation channel will generally be in the range of about 0.05 mm to 50 cm, more usually in the range of about 0.5 mm to 10 cm, and in many cases not more than 5 cm, while the various portions of the channels other than the primary channels, the peripheral channels, will be within those ranges and frequently in the lower portion of the range. The reservoirs will generally have volumes in the range of about 10 nl to 10 $\mu$l, usually having volumes in the range of about 20 nl to 1 $\mu$l. The substrate or card will generally have a thickness of at least about 20 $\mu$m, more usually at least about 40 $\mu$m, and not more than about 0.5 cm, usually not more than about 0.25 cm. The width of the substrate will be determined by the number of units to be accommodated and may be as small as about 2 mm and up to about 6 cm or more. The dimension in the other direction will generally be at least about 0.5 cm and not more than about 50 cm, usually not more than about 20 cm. The substrate may be a flexible film or relatively inflexible solid, where the microstructures, such as reservoirs and channels, may be provided by embossing, molding, machining, etc.

The microfluidic devices may be characterized by having a single unit for operations in a single structure or a plurality of units. The microfluidic devices will be characterized by having one or more operational units present in the substrate, where the number of units may vary from 16 to 1536 units, more usually not more than about 384 units, the number of units frequently being related to the number of wells in a microtiter well plate. Each unit will have at least one channel and at least two reservoirs, usually having at least two channels and at least four reservoirs. The total number of reservoirs for a device will generally be in the range of about 4 to 1600, more usually in the range of about 64 to 1500.

For sealing the substrate, and enclosing the channels in the substrate, a film sized for a single card or a continuous sealing film may be used, which may be unrolled from a reel as the devices are moved in a continuous manner, for example, on a wheel or moving belt. The films may be natural rubber, polyisoprene, ethylene-propylene elastomers, polyurethane foams, polydimethylsiloxane, etc. The films may be thin or thick, so long as they have a minimum dimension, which provides for sealing. Generally, the films will be at least about 50 g in thickness. Films may be used which have a thin adherent layer that will adhere to the surface. Useful adhesives include pressure sensitive adhesives, such as ethylene-containing polymers, urethane polymers, butyl rubber, butadiene-acrylonitrile polymers, butadiene-acrylonitrile-isoprene polymers, and the like. See, for example, U.S. Pat. No. 5,908,695 and references cited therein.

B. Polymer Composition

The polymer composition of the invention comprises a mixture of polymers of different hydrophilicity/hydrophobicity, where one component serves mainly a coating function, while the other component serves mainly a sieving function. The polymers may be homo- or copolymers, particularly having a combination of the two.

The polymers may be naturally occurring polymers, modified naturally occurring polymers, or synthetic polymers, both addition and condensation polymers. The combination of polymers will have polymers differing in their water solubility. Of particular interest are combinations of polyacrylamides, where the polyacrylamides in the mixture differ as to their substitution on the nitrogen, varying from hydrogen to substituents of from 1 to 12 carbon atoms, usually 1 to 4 carbon atoms, and may be substituted or unsubstituted, e.g., oxy, including hydroxy and ether, heterocycle, e.g. rings of from 4 to 6 annular members, with the heteroannular member being N, O or S, etc., and being mono- or disubstituted.

The synthetic polymers are substantially free of cross-linking ("linear"). The polymers are usually of at least about 20 kDal weight average molecular weight, generally at least about 50 kDal, and not more than about 25,000 kDal weight average molecular weight, usually in the range of about 50 to 18,000 kDal weight average molecular weight. The polymers will be water soluble, the water solubility differing between the sieving polymer ("more hydrophilic") and the coating polymer ("less hydrophilic"). Sieving polymers include polyacrylamides, polyethers, particularly polysaccharides, such as hydroxyethyl cellulose, agarose, and dextran; polyalkyleneoxy polymers with alkylenes of from 2 to 3 carbon atoms, particularly 2 carbon atoms, and the like. Illustrative sieving polymers include: polyacrylamide; hydroxyethylcellulose (MW 50 kDa to 1000 kDa); agarose; polyethylene glycol (20 kDa to 200 kDa); dextran; poly-N-acryloyl-tris (polyNAT); poly AAEE (poly N-acryloylaminoethoxyethanol).

Coating polymers may include homo- and copolymers, both naturally occurring, modified naturally occurring and synthetic, particularly synthetic. Among the polymers are polymers of acrylamide (including methacrylamide), substituted cellulose, where the substituents may be methyl and hydroxypropyl, individually or in combination, polyalkylene oxides, where alkylene is of from 2 to 3 carbon atoms and the terminal hydroxyls are substituted with acyl or alkyl groups of from about 1 to 18 carbon atoms, and polyvinylpyrrolidone. Of particular interest are polyacrylamides (including polymethacrylamides), either homo- or copolymers, where the nitrogen is mono or disubstituted, and the substituent groups are alkyl of from 1 to 6, usually 1 to 3 carbon atoms, heterocycles of from 4 to 6 carbon atoms, where the heteroatom is N, O or S, hydroxysubstituted alkyl of from 2 to 6, usually 2 to 4 carbon atoms and sugars linked to nitrogen by a bond or linking group of from 2 to 6 carbon atoms, having from 0 to 2 heteroatoms in the chain, particularly O, N or S. Illustrative coating homopolymers include: polydimethylacrylamide; polydiethylacrylamide; polyethylene oxide; methylcellulose; hydroxypropylmethylcellulose; hydroxypropylcellulose; and polyvinylpyrrolidone. Illustrative copolymers include copolymers of two to three, usually only two, of the following monomers: N-methylacrylamide; N-ethylacrylamide; N-ethylmethacrylamide; N-methylmethacrylamide; N-propylacrylamide; N-propylmethacrylamide; N-isopropylacrylamide; N-butylacrylamide; N-pyrrolidylmethacrylamide; N-piperidylmethacrylamide; N-acryloylaminopropanol; and N-(acryloylaminoethoxy) ethyl-beta-D-glucopyranoside.

The compositions which are employed with the combination of two polymers will generally have a weight ratio of the more soluble polymer, the sieving polymer to the less soluble polymer, the coating polymer, in the range of about 1–10:1, usually in the range of about 1–5:1, more usually 1.5–3:1, the more soluble polymer preferably being in greater amount than the less soluble polymer. When the polymer compositions are used separately, that is the channel is coated first and then the sample medium is added with the sieving polymer and optionally the coating polymer, the ratios of the amounts will vary, since the sieving polymer will be in a much larger volume. Preferably, the sample medium will contain both polymers.

The acrylamides of the subject invention are preferably derived by the polymerization of the monomer, particularly acrylamide, in the absence of a cross-linker to provide uncrosslinked, normally linear, polymer, using conventional free radical initiation in the substantial absence of oxygen. The polymers are readily produced using conventional conditions for polymerization of acrylamide polymers, conveniently using an aqueous or organic medium, depending upon the solubility of the monomer and polymer, having from about 5 to 30% (wt/vol) total monomer and a conventional free radical initiator, such as ammonium, sodium or potassium persulfate and tetramethylethylenediamine or metabisulfite, riboflavin, riboflavin-1-phosphate, methylene blue and toluene sulfinate, benzoin methyl ether, or 1-hydroxycyclohexyl phenyl ketone, usually in the substantial absence of oxygen. Conveniently, an inert detergent may be added, such as non-ionic detergents, e.g. polyoxyalkylene detergents, in the organic solvent. Detergent concentrations will generally be in the range of about 1–5% wt/vol. The catalyst concentration will vary with the particular catalyst, generally being in the range of about 0.001 to 0.1 wt/vol for each component of the catalyst, where the ratio of the components will generally be in the range of about 1–5:1 moles for the oxidant to amine. The reaction temperature will generally be in the range of about 0 to 100° C. and the time for the reaction will generally be in the range of about 1 min to 24 h, the particular conditions not being critical and varying with the other parameters. After completion of the reaction, depending on the nature of the polymer, it may be isolated in various ways, e.g. precipitation and washing, followed by evaporative removal of solvent and remaining monomer, dialysis and lyophilization, etc. The polymers will then be ready for mixing to provide the final composition.

When mixing the polymers, precipitation is to be avoided as described in the Experimental section. Buffer solutions are employed, which will be compatible with the capillary electrophoresis. Various buffer solutions may be used, where one or more buffer components are employed. Useful buffer components include Tris, borate, EDTA, MOPS, TAPS, sodium acetate, sodium citrate, potassium or sodium phosphates, glycine, bis-Tris, etc. Generally, each of the buffering components will be present in from about 0.001 to 0.5M, more usually 0.075 to 0.15M, while other components, such as EDTA, DETPA, etc., will be present in from about 0.001 to 0.005M. In addition to the other additives, a denaturing agent is conveniently employed for denaturing dsDNA when sequencing or other nucleic acid analysis, such as urea, formamide and for denaturing proteins, sodium dodecyl sulfate. The amount of the denaturing agent will vary, depending on the particular denaturing agent employed, the conditions of the electrophoresis, the composition being analyzed, and the like. Generally, the denaturing agent will be present in the range of about 0.2–50 wt/vol.

For the less water-soluble polymer, it may be necessary to mix the polymer with the solution with agitation, followed by filtration. With the more soluble polymer, centrifugation followed by filtration may be sufficient to provide a clear solution. The two solutions are then combined at a polymer weight ratio in the range of about 1–5:1, more usually 1.5–3:1. Care should be taken to prevent precipitation. Precipitation can be avoided by the stepwise careful mixing of the ingredients and then removal of sediment.

The more water-soluble polymer is conveniently a homopolymer of acrylamide or other hydrophilic neutral monomers, e.g. a homopolymer or copolymer of acrylamide and hydrophilic neutral monomers, such as 2-hydroxyethyl acrylate, N-(2-hydroxyethyl acrylamide, 2,3-dihydroxypropyl acrylate, α-hydroxymethylacrylamide, etc.). These hydrophilic polymers are better solvated by the aqueous buffer and their adsorption energy is not sufficiently high to maintain the polymer molecules adsorbed to the channel walls. The molecular weight and distribution is selected to provide the desired sieving properties. The less soluble polymer will preferably be a copolymer of N,N-disubstituted acrylamides, where the substituents are alkyl of from 1 to 3 carbon atoms, usually 1–2 carbon atoms, where the total number of carbon atoms bonded to the nitrogen is in the range of 2–6, usually 2–4. The alkyl groups will be methyl, ethyl, propyl and isopropyl. The ratio of the different monomers may be varied depending upon the degree of hydrophobicity desired. Of particular interest are N,N-dimethyl acrylamide and N,N-diethylacrylamide, namely the symmetrically substituted amides. Generally the monomer having the lower number of carbon atoms will be in a ratio to the monomer with the higher number of carbon atoms in the range of about 1–5:1, usually in the range of about 1.5–3:1, based on the composition used for preparation of the copolymer.

As indicated previously, all or portions of the subject polymers may be substituted with other polymers having the characteristics described above, namely neutral, water soluble, having the appropriate hydrophilicity/lipophilicity balance, having the appropriate adsorption energies, molecular weight, and appropriate sieving properties.

The polymer solutions may be used separately or may be combined in a single solution for coating and sieving. The combined polymer solution, particularly with a denaturant, may be used advantageously as the separation buffer for the nucleic acid separations and sequencing. Where the coating solution is used separately for coating, the concentration in each of the solutions will generally be from about 0.05 to 7.5% by weight of the polymer, with the less hydrophilic polymer being in the higher portion of the range and more hydrophilic polymer being in the lower portion of the range. Generally the less hydrophilic polymer will be present in the solution in about 2.5 to 7.5%, more usually 3 to 6%, while the more hydrophilic polymer will be present in from about 0.1 to 4%, more usually 1 to 3%. When the solutions are combined, less of the more hydrophobic polymer is required, where the concentration will be in the range of about 0.05 to 1, more usually 0.1 to 0.5, while the more hydrophilic polymer will be present in an amount in the range of about 0.5 to 5%, more usually 0.5 to 3%. The buffer will usually be at about 0.1 to 5M, while the denaturing agent will generally be in the range of about 1–10M. The mole ratio of the polymers will generally be in the range of about 2–20:1, more usually 5–15:1, and may vary at to which polymer is in greater amount depending upon whether a mixed solution or individual solutions are employed.

C. Coating and Electrophoresis Methods

The polymer solutions will be applied to the separation channel in the microfluidics device, separately or in combination. When applied separately, the less hydrophilic polymer solution will usually be added first, followed by washing and addition of the more hydrophilic polymer solution, followed by washing. One or both of the additions of polymer solutions may be repeated, particularly the addition of the more soluble polymer. Regeneration with the less hydrophilic polymer need not be repeated after each run.

In preparing the separation channel in the microfluidics device, the channel may be first coated with the less hydrophilic polymer composition by passing the solution through the channel. Usually, the solution will be allowed to remain in the channel for a short time, usually not more than about 10 minutes and at least about 1 minute. After sufficient time for the polymer to coat the walls, the channel is washed with a convenient liquid, e.g. water, particularly deionized water. The amount of water used to flush the channel will depend on the size of the channel and is primarily one of convenience. Capillary action will move the water through the channel, although mild pressure may also be used. The more hydrophilic polymer solution is then added under similar conditions to that used previously, followed by washing and the coating may be repeated with the more hydrophilic polymer solution. Alternatively and preferably, one may combine the two polymers and coat the channel simultaneously, using the same time frames as indicated for the individual solutions.

Once the channel has been coated it is ready to be used for capillary electrophoresis. Various processes may be performed in the channel, as previously described.

In performing the operations with the device, after coating the channels with the polymer composition, the device will be filled with the appropriate buffer. Depending on the nature of the operation, one or more reservoirs may be connected by channels proximal to one end of a channel. For descriptions of channel networks, see, for example, WO96/04547. The sample may be introduced into one reservoir and other components of the operation introduced into the same or different reservoirs. Electrodes are placed in the appropriate reservoirs to provide potential gradients between reservoirs for movement of ions. During the course of the operation, the direction, and voltages may be changed. The sample and other components may then be introduced into a channel. In many situations there will be a second channel providing an intersection with the first channel with a first channel to into which the sample is directed. Alternatively, the first channel may join at a tee with a second channel and a third channel intersecting at a tee with the second channel or other designs for enhancing the sharpness of the sample plug for analysis. In both situations, the sample may be pinched at the intersection or between the two channels joining the second channel, respectively and then injected downstream into the second channel. In this way the sample may be contained in a small volume as it moves down the channel for analysis. In many situations components of the sample are separated and desirably each component is maintained in a small volume for analysis.

The following examples are offered by way of illustration and not by way of limitation.

EXAMPLE 1 CHIP LAYOUT

Plastic microfluidics devices are produced by hot embossing with a nickel electroform master containing the desired electrophoresis pattern. The electrophoresis device includes a double tee injector and a main separation microchannel. The double tee injector has a gap of 250 μm that intersects with the main separation channel (FIG. 8). The distance from the center of the injector to the detection point is about 18 cm. Four accessing reservoirs containing buffer, sample waste buffer, waste buffer and sample are about 1.5 mm in diameter. 1–4 denotes for the buffer reservoir, the sample reservoir, the waste buffer reservoir and the sample waste reservoir, respectively. The plastic microchips are made of poly(methylmethacrylate) (PMMA) or Zeonor.

EXAMPLE 2 GENESCAN 700 DNA LADDER

GeneScan 700 DNA ladder is a set of specially engineered DNA fragments labeled with a fluorescent dye (TET, 6-carboxy-4,7,2',7'-tetrachlorofluoroscein, emission wavelength: 540 nm; excitation wavelength: 520 nm). GeneScan 700 contains 20 fragments including 35 bp, 50 bp, 75 bp, 100 bp, 139 bp, 150 bp, 160 bp, 200 bp, 250 bp, 300 bp, 340 bp, 350 bp, 400 bp, 450 bp, 490 bp, 500 bp, 550 bp, 600 bp, 650 bp, and 700 bp. Under the experimental condition used, only 18 fragments are observed which excludes 35 bp and 50 bp due to the interference of small fluorescent fragments co-migrating in this region. The loading sample is prepared with 5 μ GeneScan 700, 5 μl deionized water, and 10 μL deionized formamide. The loading sample is then denaturated at 95° C. for 2 minutes before chilling in an ice bath.

EXAMPLE 3 SEPARATION CONDITIONS

The sieving matrix is loaded from buffer waste reservoir (3) by applying 150 or 200 psi for 2 or 5 minutes. After being loaded with sample and buffer for the rest of the reservoirs, the whole microchip is placed on a thermal station and heated to 35° C. A Peltier device thermally controls the thermal station. The four-color detection system has been disclosed in provisional patent application Ser. No. 60/133,727, filed May 12, 1999. The data acquisition rate is about 10 Hz while a 488 nm Ar ion laser is used with a laser power of about 7 mW. The separation field strength is about 150 V/cm. The voltage setup is listed in the following table:

| Notation Name | 1 Buffer Well | 2 Sample | 3 Buffer Waste | 4 Sample Waste | time(s) |
|---|---|---|---|---|---|
| pull through | 0 | 0 | 0 | 500 | 90 |
| relaxation | 0 | 0 | 0 | 100 | 20 |
| separation | 0 | 310 | 3020 | 300 | 10000 |

EXAMPLE 4. PREPARATION OF LDD30 HYDROPHOBIC COPOLYMER

The LDD30 polymer is a non-crosslinked polymer synthesized by free-radical solution polymerization. The polymerization is carried out in an aqueous solution of the monomers, diethylacrylamide and dimethylacrylamide (30:70). The total concentration of monomers is about 10% or less (w/v). The solution is de-gassed before synthesis by bubbling argon, helium, or nitrogen. Polymerization is initiated by addition of ammonium persulfate and TEMED (tetramethylethylenediamine). This solution is subjected to dialysis against purified water and freeze-drying to remove unreacted monomer and to obtain the polymer in solid form.

LDD30 is a composition defined as 30% diethylacrylamide, 70% dimethylacrylamide by weight, where the percentages are expressed as a percent of the total mass of monomers in the solution before polymerization. This composition has been found to have desirable separation and coating properties. Polymers with other ratios of the two monomers can be useful, depending upon the performance requirements. The extent of incorporation of each monomer into the resulting polymer has not been assayed.

EXAMPLE 5 PREPARATION OF 4.5% (w/w) LDD30 (MW 2 MILLION), 7M UREA, 1×TBE SOLUTION (25 g)

1. Prepare a 10×TBE solution (0.89M Tris, 0.89M borate and 0.02M EDTA) by weighing 1.7 g of 1×TBE dry powder (ultra pure grade; Amresco, Solon, Ohio) and dissolving it to a final volume of 100.00 mL using MilliQ water (18 ohms) and a 100.00 mL-volumetric flask.

2. Weigh 11.875 g of MilliQ water in a clean dry 40 mL-glass vial.

3. Weigh 9.5 g of urea (ultra pure grade, USB, Cleveland, Ohio) on weighing paper. Add the urea to the vial already containing the water. Cap the vial and manually shake it until all the urea is dissolved.

4. Add 2.5 mL of 10×TBE solution to the vial using a graduated pipet. Shake the solution to mix well.

5. Weigh 1.125 g of LDD30 on weighing paper and add it to the vial.

6. In order to dissolve the LDD30, the solution is left overnight shaking in a Labquake shaker (Labindustries, Berkeley, Calif.).

7. The following day, the foamy solution is filtered through a 5 μm-nylon filter (Cameo25NS, Osmonics) using a syringe and nitrogen gas pressure. The filtrate is collected in a clean dry glass vial.

8. The filtered solution is then degassed by centrifuging it for 30 min at 1,000 rpm using a Beckman GS-6 centrifuge (Palo Alto, Calif.).

9. The degassed solution is stored at 4° C. to prevent the degradation of urea.

EXAMPLE 6 PREPARATION OF LPA (LINEAR POLYACRYLAMIDE) HYDROPHILIC POLYMER

The polymerization was performed according to the protocol described in Eur. Polym. J. 1984, 20, 505–512 with slight variations. In a Pyrex reaction flask, a 40% w/w solution of acrylamide was dispersed in a solution of 2.4% SPAN 80 in petroleum special to a volume ratio of 1:1. APDS and TEMED were used to catalyze the reaction, both at a final concentration of 0.0055 w/v. To remove oxygen, the entire dispersion was purged continually with nitrogen, and then the polymerization reaction was performed at 35° C. Acetone was used to precipitate the polyacrylamide. The precipitate was washed several times with acetone on a Buechner funnel, and residual solvent was removed under oil-pump vacuum on a rotary evaporator. To prepare 2%

LPA matrix solution for DNA sequencing, the dry polymer, urea, buffer concentrate, and water were added to the desired concentrations in a glass jar and then slowly stirred with a magnetic bar.

EXAMPLE 7 PREPARATION OF MIXED SIEVING MATRIX FROM LDD30 AND LPA

Procedure to prepare 2% (w/w) LPA010, 0.2% (w/w) LDD30, 1×TTE, 7M urea solution (5 g)

1. Prepare a 10×TTE solution (0.5 M Tris, 0.5 M TAPS and 0.02 M EDTA) by dissolving the following with MilliQ water in a 25.00 mL-volumetric flask:
   - 1.5144 g of Tris base (Pharmacia Biotech, Uppsala, Sweden)
   - 3.0412 g of TAPS (ultra pure grade, Sigma, St, Louis, Mo.)
   - 0.1861 g of disodium EDTA (Pharmacia Biotech, Uppsala, Sweden)
2. Weigh 2.49 g of MilliQ water in a clean dry 20 mL-glass vial.
3. Weigh 1.90 g of urea (ultra pure grade, USB, Cleveland, Ohio). Add the urea to the vial already containing the water. Cap the vial and manually shake gently until all of the urea is dissolved.
4. Add 500 $\mu$L of 10×TTE solution to the vial using a pipetman. Shake the solution gently to mix well.
5. Weigh 0.010 g of LDD30 and add it to the vial.
6. Weigh 0.100 g of LPA010 and add it to the vial.
7. Gently shake the vial to mix all contents. Then centrifuge the vial for 15 min at 1,000 rpm using a Beckman GS-6 centrifuge (Palo Alto, Calif.). All the contents should be at the bottom of the vial.
8. Stir the solution overnight using a Corning magnetic stirrer set at its minimum speed (60 rpm).
9. The following day, the foamy solution is filtered through a 5 $\mu$m-nylon filter (Cameo25NS, Osmonics) using a syringe and nitrogen gas pressure. The filtrate is collected in a clean dry glass vial.
10. The filtered solution is then degassed by centrifuging it for 60 min at 1,000 rpm using a Beckman GS-6 centrifuge (Palo Alto, Calif.).
11. The degassed solution is stored at 4° C. to prevent the degradation of urea.

EXAMPLE 8 PREPARATION OF SEQUENCING SAMPLE LADDERS

DNA sequencing reactions were conducted using standard cycle sequencing chemistry with AmpliTaq-FS and BigDye terminator (Applied Biosystems/Perkin-Elmer Corp., Foster City, Calif.) on an M13mp18 single-stranded template (Amersham/USB). M13 universal primers (−21) are used in all the reactions discussed below. The temperature cycling protocol for this sequencing chemistry was performed on a PE 2400 thermocycler (Applied Biosystems/ Perkin-Elmer Corp., Foster City, Calif.), containing 30 cycles of 96° C. for 10 sec, 50° C. for 5 sec, and 60° C. for 4 min in 20 $\mu$L of total volume. After completion of the reaction, the samples were rapidly cooled to 4° C. and held at that temperature until ready to purify.

Sequencing reaction products were purified using a Centri-Sep spin column (Princeton Separations) to remove the dye-labeled terminators and salt contents. Then 10 $\mu$L of the purified sequencing products was added with 10 $\mu$L deionized formamide, for denaturating at 95° C. for 2 min. After the 20 $\mu$L solution is chilled to 4° C., it is loaded on to plastic microchips. The sample is then loaded in the sample reservoir of a microfluidics chip.

EXAMPLE 9 CROSSOVER PLOT FOR DATA ANALYSIS

Crossover plots of peak interval and peak width were plotted against DNA fragment size. The peak interval is the spatial distance between two DNA fragments differing by one nucleotide in length. The peak width refers to the full width at half peak height maximum (FWHM). The point where the two lines cross over indicates the single base resolution limit of the separation and corresponds to a resolution value of 0.59. The peak widths were measured using the Blue channels. The peak widths were fitted to a second-order polynomial. The data was base-lined and analyzed with crossover tool software from PE Biosystems.

EXAMPLE 10 EOF COMPARISON

In Table I is compared the electroosmotic mobility on different surfaces. EOF on an uncoated glass chip is 37.4× $10^{-5}$ cm$^2$/V sec. If the glass channel surface is coated with linear polyacrylamide with a minor modification of the Hjerten procedure (Hjerten, S. J. Chromatogr. 1985, 347, 191–198), the EOF is reduced to less than 1×10$^{-5}$ cm$^2$/V sec. However, after extensive use of the same channel for several months, the EOF became 2.6 or 10×10$^{-5}$ cm$^2$/V sec in two different cases. The same materials, such as V825, used in different methods, hot embossing or injection molding, for preparing the microfluidic devices can cause slightly different electro osmotic flow. Even changing the process conditions can cause a change in EOF. It is seen in Table I that a 4.5% LDD30 solution can substantially reduce the EOF simply by flushing this polymer solution into the microchannel.

All EOF measurements were done with 1× TTE as buffer, Rhodamine B as EOF marker, and at room temperature. The sample is placed in the buffer waster reservoir (3) and the distance traveled and time taken of this sample after the voltage is applied was measured to determine the EOF for each case. The liquid level is kept at the same height to avoid hydrodynamic flow. The EOF data in Table 1 was obtained after surface treatment with 2% LPA10 and 0.2% LDD30 polymer matrix.

TABLE I

Electroosmotic Mobility (EOF) on Different Surfaces

| Type of chip | $\mu e$ of ($10^{-5}$ cm$^2$/V sec) |
|---|---|
| Uncoated glass chip | 37.4 |
| Glass chip newly coated with LPA | <1 |
| Glass chip with degraded LPA coating | 2.6, 10 |
| Chip (V825-V825) by hot embossing | 9 (±3) |
| Chip (V825-V825) by injection molding | 10 (±1) |
| E-102199-1 (PID #6) (ICI-ICI) | 15 (±2) |
| E-110299-1 (PID #7) (ICI-ICI) | 22 (±3) |
| E-110299-1 (ICI-ICI) coated with LDD30 | 2.1 (±0.9) |
| E-112999-1 (ICI-MT40-ICI) sandwich chip | 9.8 (±0.1) |
| E-112999-2 sandwich chip coated with LDD30 | <1 |
| Zeonor 1420-Zeonor 1020-Zeonor 1420 chip coated LDD30 | 3.4 (±1.2) |
| Zeonor 1420-Zeonor 1020-Zeonor 1420 | 20 (±3) |

Sources of plastic materials: V825, Mitsubishi (MT40); Rohm 99553, ICI; Elf Atochem, Atoglas Division, 200

Market St. Philadelphia, Pa. 19103; Cyro, 100 Enterprise Dr., Rockaway, N.J. 07866; Polymer Extruded Products, 297 Ferry St., Newark, N.J. 07105; Mitsubishi Materials, Tokyo, Japan; Rohm & Haas, 100 Independence Mall W. Philadelphia, Pa. 19106; Union Carbide, Old Ridgebury Rd., Danbury, Conn. 06817; Imperial Chemical Industries, ICI Group Headquarters, London SW1P 3JF, UK; Nippon Zeon, Furukawa Sogo Building, 2-6-1 Marunouchi, Chiyoda-ku, Tokyo 100.

EXAMPLE 11 SURFACE COATING PROCEDURE COMPARISON

Figure 1A:
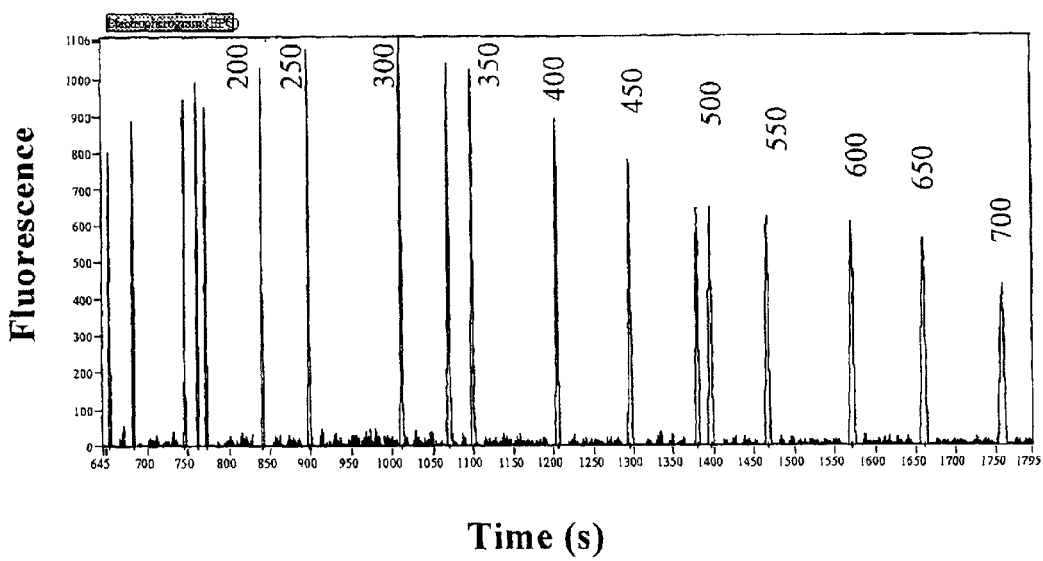
FIGS. 1A and 1B are an electropherogram of a DNA separation of a DNA ladder using a single polymer (FIG. 1A) and a graph of the separation interval (FIG. 1B).
Figure 1B:
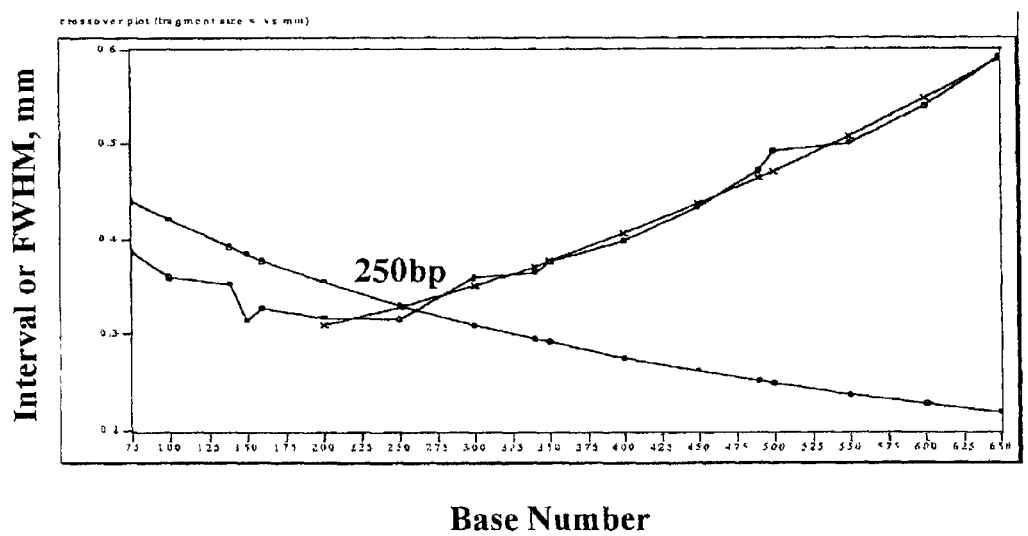

FIG. 1 shows the DNA separation and its crossover plot of GeneScan 700 on an uncoated PMMA microchip with 2% LPA in 1× TTE and 7M urea solution. The microchannel was rinsed with deionized water before loading the sieving matrix. Due to the EOF associated with an untreated PMMA surface, the crossover point is only 250 bp, meaning that it only sequences up to 250 bp with the resolution of 0.59. The full width at half maximum (FWHM) increases with the length of DNA fragments, strongly suggesting that both EOF and interaction with the channel wall affect this separation.

Figure 2A:
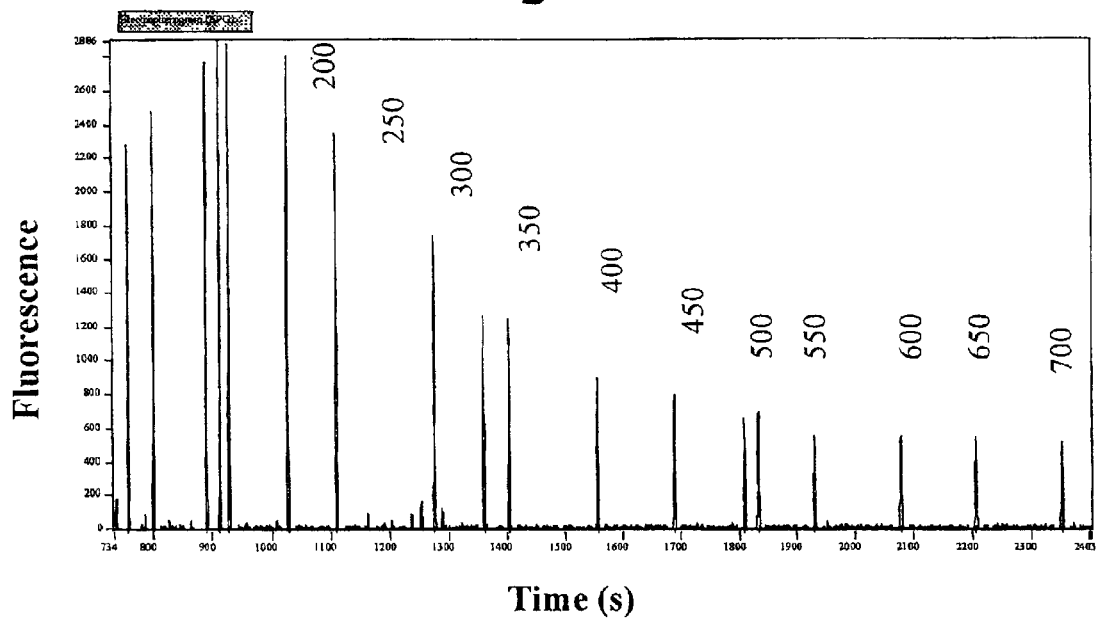
FIGS. 2A and 2B are an electropherogram (FIG. 2A) and graph of separation interval (FIG. 2B) using a composition according to this invention.
Figure 2B:
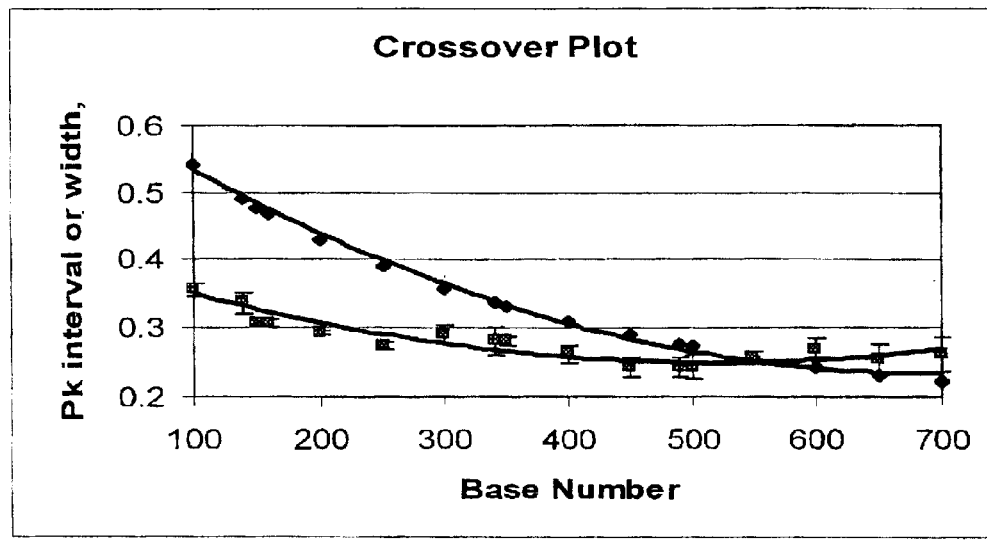

FIG. 2 shows the DNA separation and its crossover plot of GeneScan 700 on the PMMA microchip pre-treated with 4.5% LDD30 polymer in 1× TBE 7M urea buffer, using the same 2% LPA polymer in 1× TTE buffer with 7M urea as a precoating. After a single treatment with 4.5% LDD30 solution, the microchannel has been consecutively used three times. The crossover plot generated from three runs shows that both peak interval and FWHM are very consistent and a crossover point of 550 bp is obtained. The migration times for run-to-run are very similar, indicating the adsorption coatings are very stable and allow multiple runs for a single coating procedure.

Figure 3A:
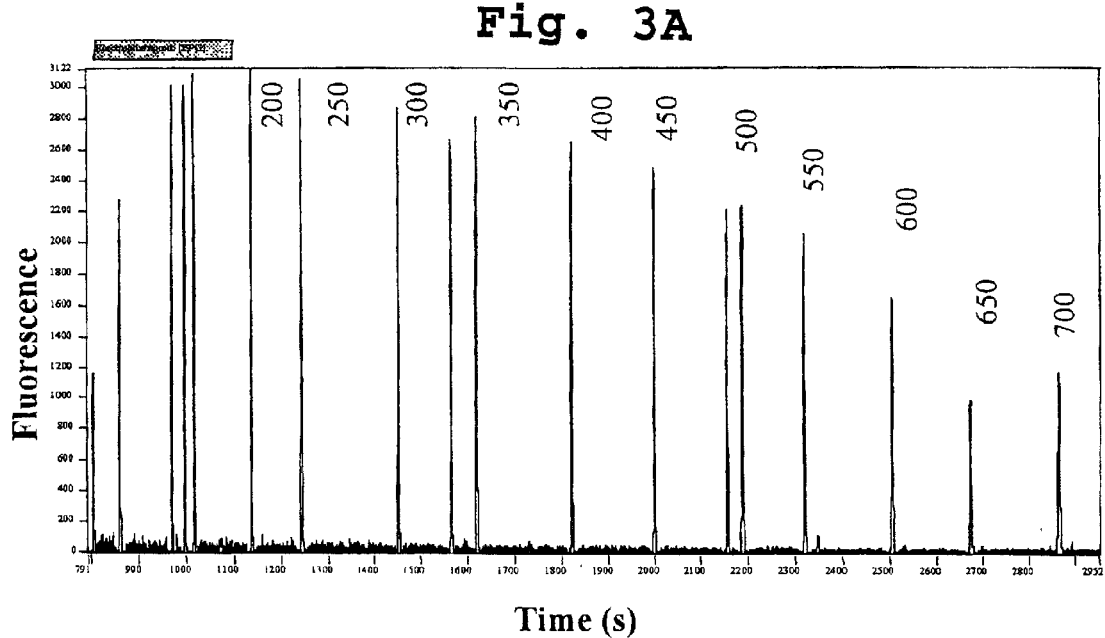
FIGS. 3A and 3B are an electropherogram (FIG. 3A) and graph of separation interval (FIG. 3B) using a different composition from FIG. 2 according to this invention.
Figure 3B:
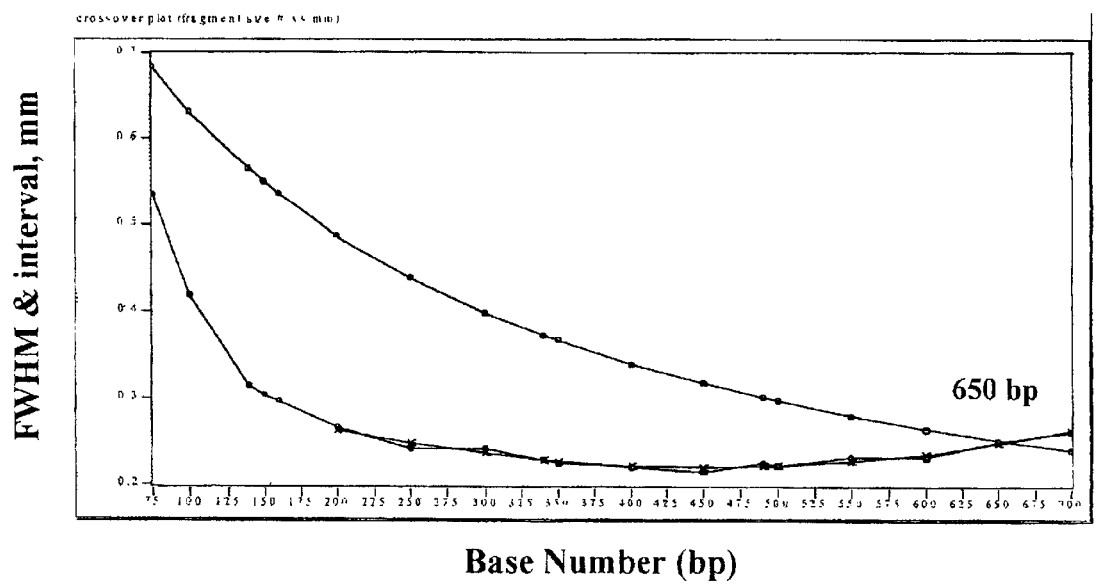

FIG. 3 shows GeneScan 700 separation and its crossover plot on bare PMMA microchip with 2% LPA sieving polymer and 0.2% LDD30 in 1× TTE 7M urea buffer. The crossover point with this sieving matrix is 650 bp, meaning that sequencing up to 650 bp is possible with this treatment. By blending the two polymers with different properties, the reduction of DNA sequencing cost can be clearly seen, due to the increase in reliability, the elimination of the covalent coating process and regeneration procedure, and the increase in useful lifetime of a capillary.

EXAMPLE 12 COATING STABILITY

Figures 4A, 4B, 4C:
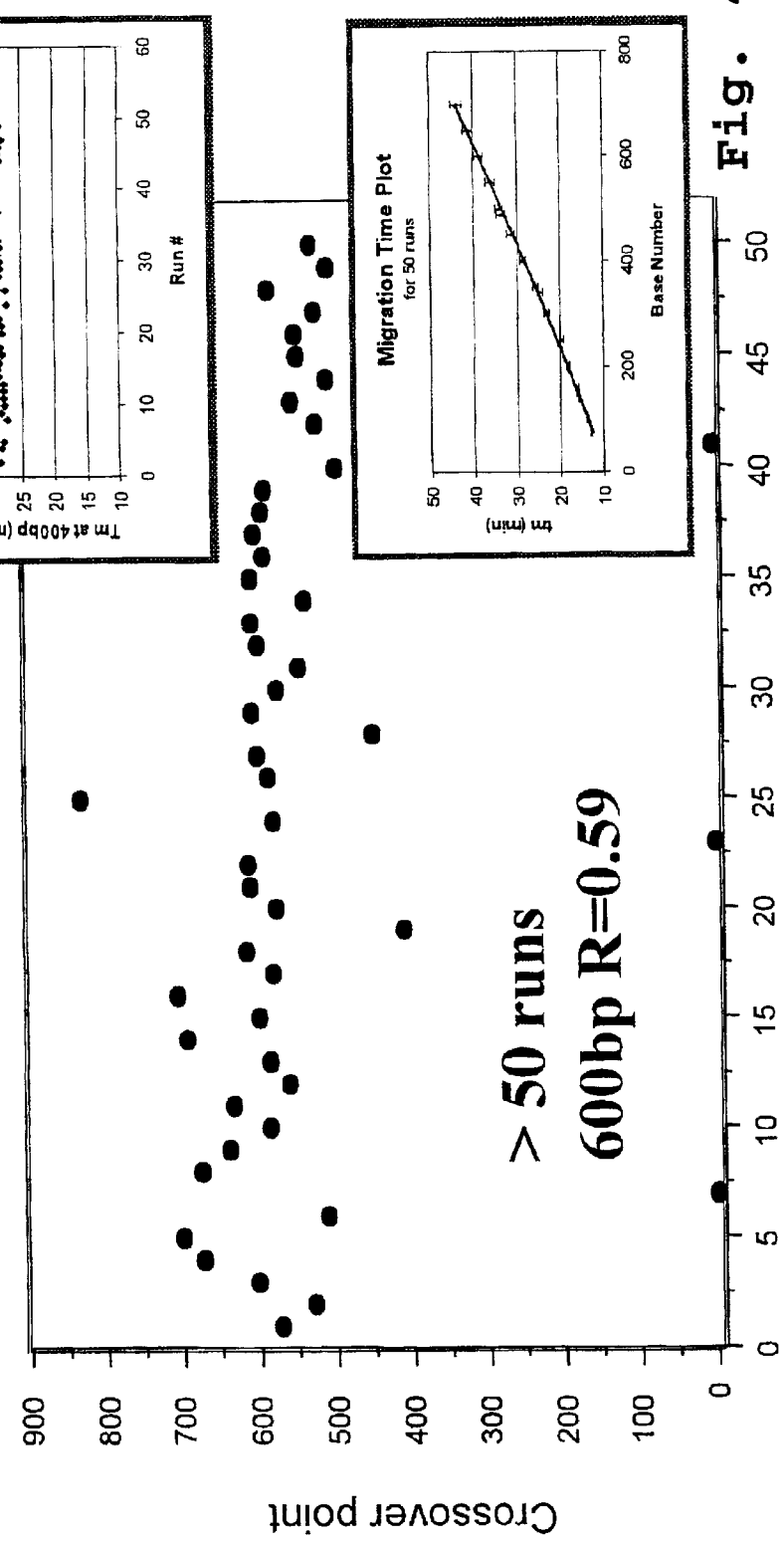
FIGS. 4A–4C illustrate the reproducibility of GeneScan 700 on untreated PMMA microchips with 2% LPA and 0.2% LDD30 in 1× TTE 7M urea buffer, showing the cross-over points as a function of run number (FIG. 4A), the migration time at 400 bp as a function of run number (FIG. 4B), and the migration time as a function of fragment size (FIG. 4C).

FIG. 4 shows the reproducibility of GeneScan 700 on untreated PMMA microchips with 2% LPA and 0.2% LDD30 in 1× TTE 7M urea buffer. This experiment also reflects the lifetime of the PMMA microchips for DNA sequencing. 50 runs were performed. The average crossover point for 50 runs is 600 bp. The migration times for all the fragments are very consistent.

Figure 5:
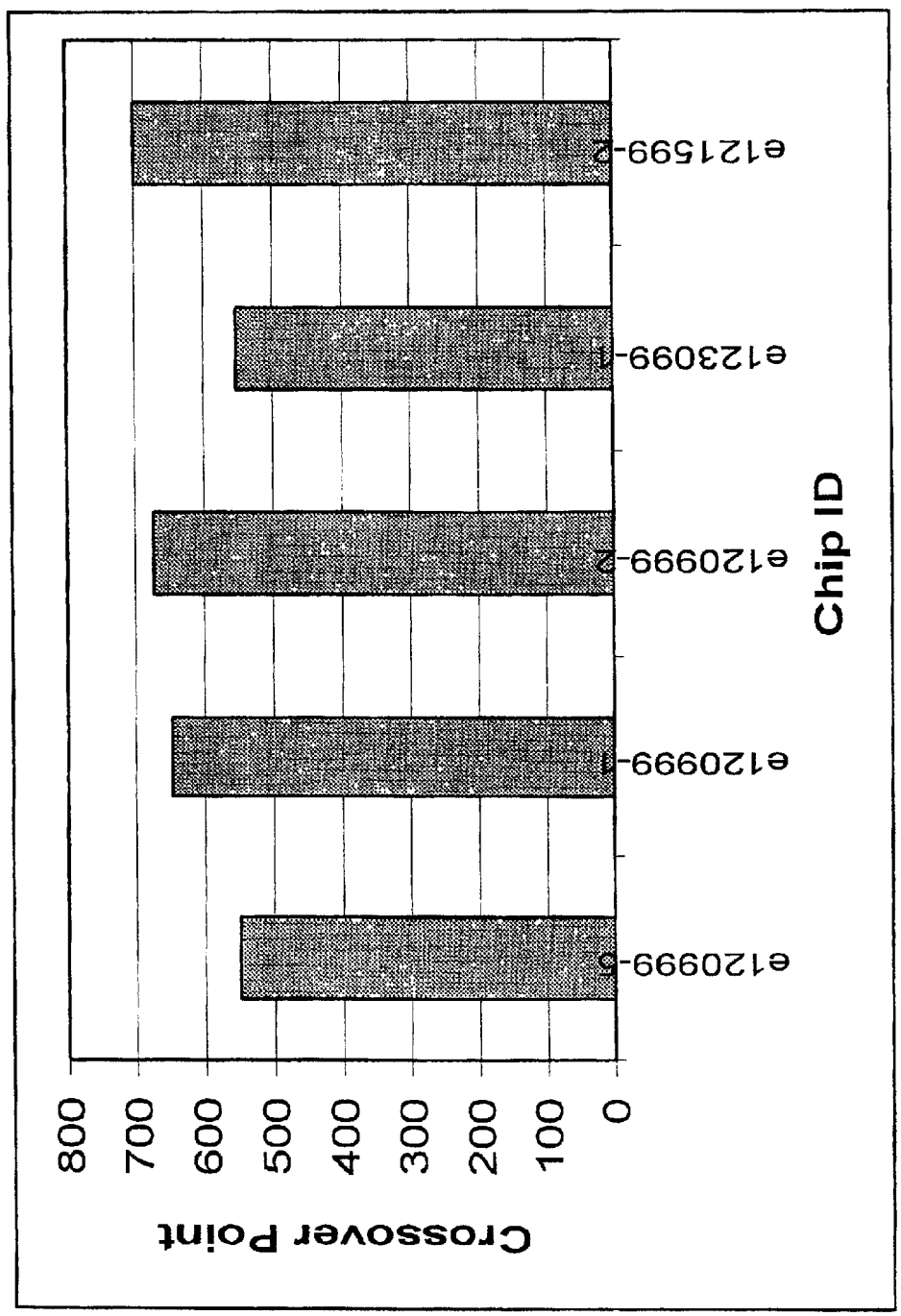
FIG. 5 is a bar graph of the reproducibility of DNA separation using different chips for the separation.
Figure 6A:
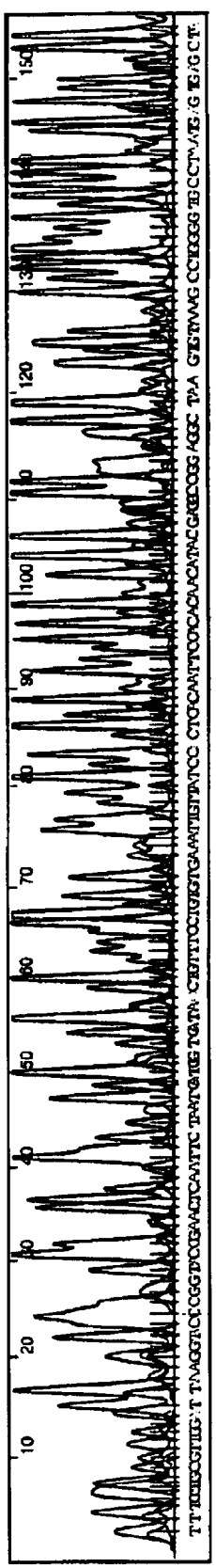
FIGS. 6A–6F are four-color sequence electropherograms demonstrating the ability to identity over 700 bases.
Figure 6B:
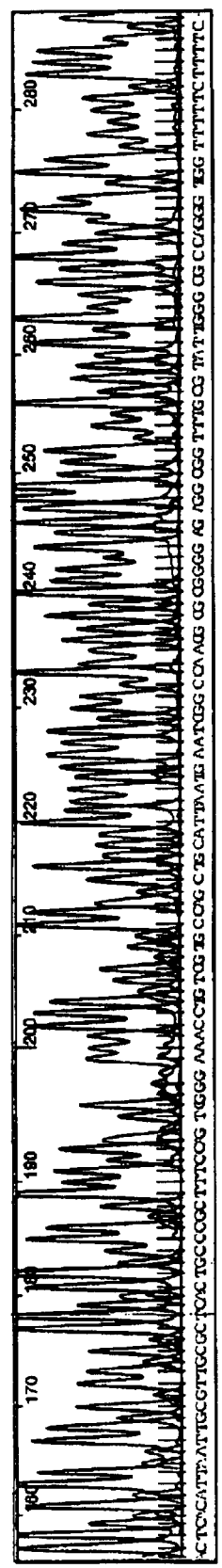
Figure 6C:
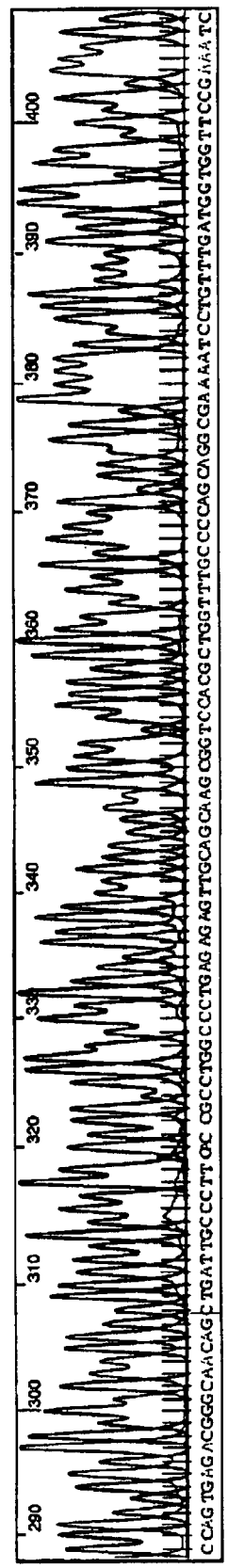
Figure 6D:
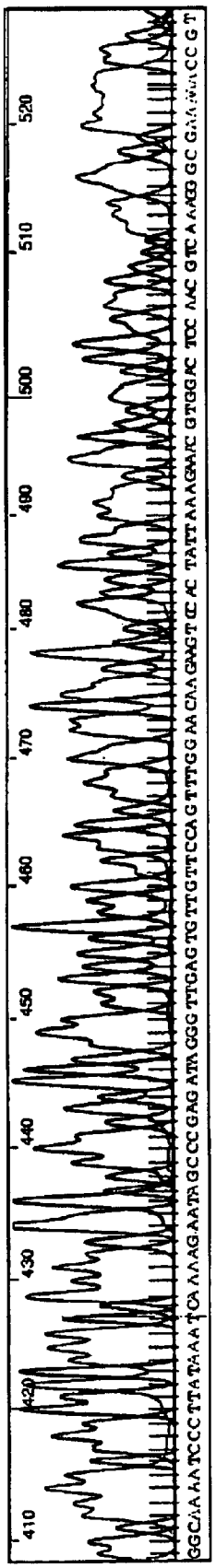
Figure 6E:
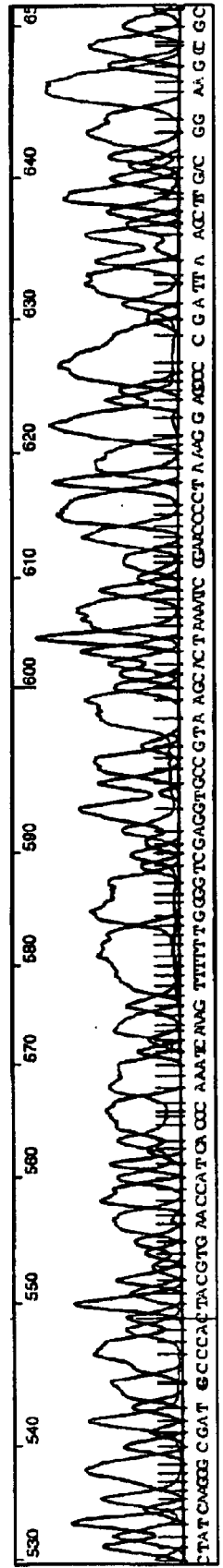
Figure 6F:
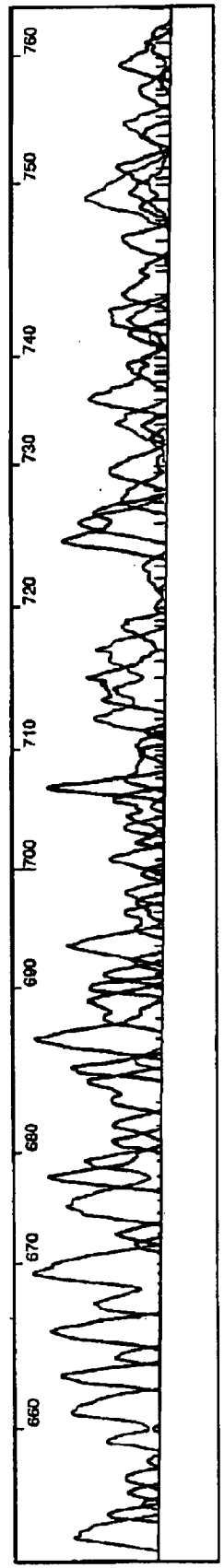

FIG. 5 shows the reproducibility of PMMA chip manufacture process. The five chips are from three different batches manufactured at different times with slightly different processes. It illustrates that the coating is stable for the PMMA chips from different batches.

To test the stability of THE dynamic coating polymer (LDD30) and the reusability of Zeonor microfabricated surface for DNA analysis, the microchannel was refilled with the mixed polymer solution repeatedly. GS700 ss DNA ladder and real 4-color DNA sequencing ladder are injected into this microchannel for separation, typically three or four real sequencing samples followed by one or two GS700 ladders.

An uncoated Zeonor microchannel with a dimension of 120 um top×50 um bottom×50 um high was first washed with about 10 column volume of methanol and then rinsed with about 10 column volume of deionized water for the first run. Starting from the second run, the mixed sieving polymer solution is filled into the microchannel by a polymer-to-polymer refill process. The microchip is set on a thermal station with a small window opened at the bottom of the base plate, which allows the detection laser reaching this microchannel. The operating temperature is set at 60 C. throughout the experiment. By operating at high temperature, the dynamic coating stability was stressed.

The separation of mixed sieving medium or matrix was prepared by dissolving poly(dimethylacrylamide) pDMA, linear poly(dimethydiethylacrylamide) LDD30 and urea into 10× TTE buffer and water to produce a sieving solution of 2.3% w/v pDMA, 0.2% w/v LDD30, 7M urea and 1×TTE (50 mM Tris, 50 mM TAPS, 2 mM EDTA). Due to the urea occupied relative large volume, water is added in the last step to ensure the accurate volume measurement for this sieving solution. The sieving solution is passed through a 0.45 um filter to remove the dust after dissolving completely. 75 runs for separating GS700 and real 4 color sequencing ladder were performed in a single 18-cm Zeonor channel. The crossover point (resolution about 0.6) for these runs kept relatively constant around 400 bp±25 bp, which is very typical for the sieving matrix and temperature, 60 C. Electrophoregrams of run #3, #33, and #75 for GS700 sample were shown in FIG. A1. The migration times are still similar throughout the stress testing. With the dynamic coating polymer LDD30 added into the sieving polymer, Zeonor microchannel is reuseable for complicated DNA samples.

EXAMPLE 13 FOUR-COLOR DNA SEQUENCING

FIG. 6 shows a four-color, electrophoretic separation of single-stranded DNA sequencing fragments generated from M13mp18 template using BigDye-labeled terminators with the blended polymer solution coating under the exactly same experimental condition. The total electrophoresis time is approximately 40 minutes and base-calling accuracy is 98% up to 640 bases. Raw DNA sequencing data traces were reduced and base-called using the program, BaseFinder, provided by Lloyd Smith's lab. BaseFinder uses a set of modules, each with user-input parameters, to define a script that can be saved and used on multiple runs. The data were treated first by baseline correction and then reduced by performing a multicomponent matrix transformation to correct for spectral cross talk.

EXAMPLE 14—UNIVERSAL COATING CONCEPT

Figure 7A:
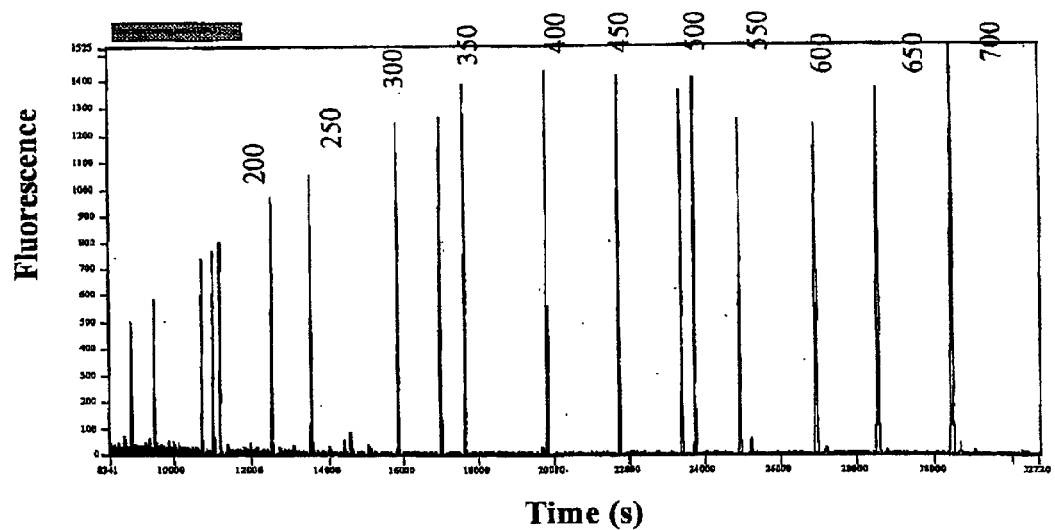
FIGS. 7A and 7B are an electropherogram (FIG. 7A) and graph of separation interval (FIG. 7B) using a different chip composition from FIGS. 1–3.
Figure 7B:
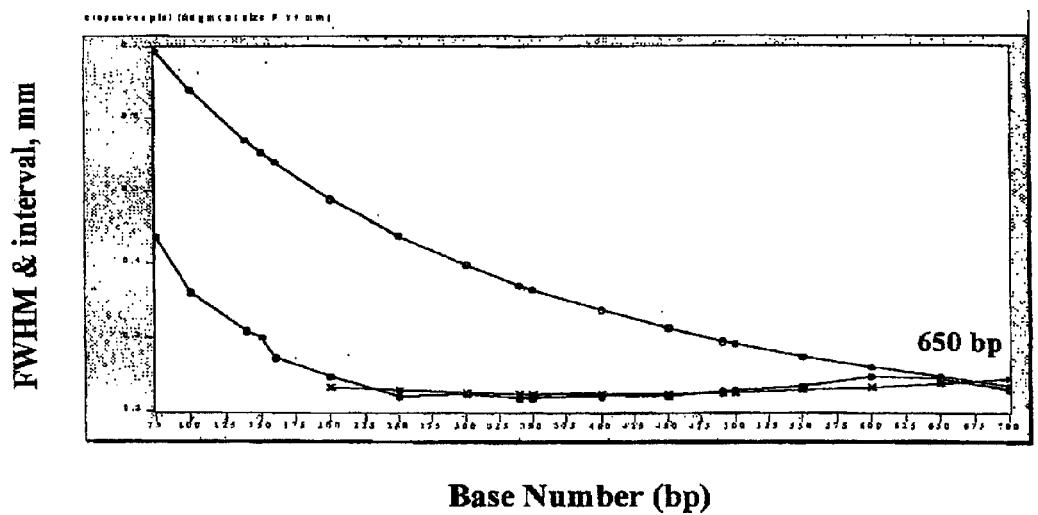

The subject polymeric blends are applicable to many other surfaces besides PMMA. Zeonor, borofloat glass and fused silica surfaces were tested. DNA sequencing on uncoated fused silica surface with LPA polymer has never been achieved. FIG. 7 shows DNA separation of GeneScan 700 on an untreated Zeonor microchip with the blended polymer solution. The crossover point reaches 640 bp in this case. FIG. 8 shows the DNA sequencing result with M13mp18 as template and BigDye terminator chemistry on Zeonor microchip using the blended polymer solution. The base-calling accuracy with BaseFinder is 98% up to 640 bp. Although the Zeonor material is quite hydrophobic compared with the other materials, DNA sequencing with real biological samples can still be performed. To obtain comparable results, N,N-dimethyl acrylamide homopolymer (Polysciences, Warrington, Pa.; 18976) may be employed in place of the acrylamide homopolymer.

It is evident from the above results that substantial advantages reside with the use of the combination product as a coating medium for channels in microfluidic devices to be used for DNA analysis. The polymers are readily prepared by conventional processes and can be mixed to provide a stable solution. The solution is easily applied to the channels to provide a stable coating that can be used repeatedly in nucleic acid determinations. In addition, as compared to the uncoated surface, one obtains greatly improved separations for DNA sequencing with the coated surface, where the two polymers are coated simultaneously.

All publications and patent applications mentioned in this specification are indicative of the level of skill of those skilled in the art to which this invention pertains. All publications and patent applications set forth herein are incorporated by reference to the same extent as if each individual publication or patent application was specifically and individually indicated to be incorporate by reference.

The invention now having been fully described, it will be apparent to one of ordinary skill in the art that many changes and modifications can be made thereto without departing from the spirit or scope of the appended claims.

What is claimed is:

1. An electrophoresis channel sieving and coating composition, for use in a microfluidics device, comprising: a buffered aqueous solution of from about 0.05 to 7.5 wt % each of a sieving polymer and a channel coating polymer in a weight ratio of 1–10:1, wherein said coating polymer is less water soluble than said sieving polymer.

2. The composition of claim 1, wherein the coating polymer is a copolymer of N-substituted acrylamide.

3. The composition of claim 2, wherein the coating polymer is a co-polymer of diethylacrylamide and dimethylacrylamide.

4. The composition of claim 3, wherein the weight ratio of the diethylacrylamide to dimethylacrylamide is in the range of about 1.5–3:1.

5. The composition of claim 1, wherein said sieving polymer is selected from the group consisting of acrylamides and methacrylamides.

6. The composition of claim 5, wherein the sieving polymer is a linear acrylamide or N,N-dimethylacrylamide homopolymer of from 500–5,000 kDal average molecular weight, and the coating polymer is a linear copolymer of two different N,N-dialkylacrylamides, wherein the alkyl groups are methyl, ethyl or propyl groups.

7. The composition of claim 1, which further includes a dsDNA denaturing agent.

8. The composition of claim 1, which includes a Tris, borate, or TAPS buffer, at a concentration in the range of about 0.025 to 0.2M.

9. A method of carrying out repeated electrophoretic separations on a polymer substrate in an electrophoretic device, comprising adding the polymer solution of claim 1 to a microfluidics device having a polymer substrate with a separation channel formed therein, performing an electrophoretic separation in said channel, replacing the polymer composition in the channel with the same polymer composition, and repeating said performing and replacing steps.

10. The method of claim 9, wherein said performing step is performed at a temperature of between 50–60.degree. C.

11. A microfluidics electrophoresis device comprising a polymer substrate having a separation channel formed therein, contained within said channel, a composition comprising a buffered aqueous solution of from about 0.05 to 7.5% by weight each of a sieving polymer and a channel coating polymer in a weight ratio of 1–10:1, wherein said coating polymer is less water soluble than said sieving polymer.

12. The device of claim 11, wherein said substrate is formed of PMMA or a cyclic olefin polymer, and said coating polymer is a copolymer of N-substituted acrylamide.

13. The device of claim 12, wherein the coating polymer is a co-polymer of diethylacrylamide and dimethylacrylamide.

14. The device of claim 13, wherein the weight ratio of the diethylacrylamide to dimethylacrylamide is in the range of about 1.5–3:1.

15. The device of claim 14, wherein the substrate is farmed of a cyclic olefin polymer, and the weight ratio of the diethylacrylamide to dimethylacrylamide is in the range of about 1.5–3:1.

* * * * *